United States Patent
Jones, Jr. et al.

(10) Patent No.: US 7,044,130 B2
(45) Date of Patent: May 16, 2006

(54) ADJUSTABLE NASAL MASK

(75) Inventors: Allan R. Jones, Jr., Derry, PA (US); Nicholas J. Macmillan, Greensburg, PA (US); Terry M. Birchler, New Albany, OH (US)

(73) Assignee: Sunrise Medical HHG Inc., Longmont, CO (US)

( * ) Notice: Subject to any disclaimer, the term of this patent is extended or adjusted under 35 U.S.C. 154(b) by 0 days.

(21) Appl. No.: 10/786,524

(22) Filed: Feb. 25, 2004

(65) Prior Publication Data
US 2004/0216746 A1 Nov. 4, 2004

Related U.S. Application Data

(60) Provisional application No. 60/451,113, filed on Feb. 28, 2003.

(51) Int. Cl.
*A62B 18/02* (2006.01)
*A62B 18/08* (2006.01)
(52) U.S. Cl. .............................. 128/206.21; 128/207.11
(58) Field of Classification Search ........... 128/201.22, 128/201.23, 202.27, 205.25, 206.12, 206.13, 128/206.18, 206.21, 206.23, 206.24, 206.26, 128/206.27, 206.28, 207.11, 207.13, 207.18, 128/DIG. 26
See application file for complete search history.

(56) References Cited

U.S. PATENT DOCUMENTS

| | | | |
|---|---|---|---|
| 5,662,101 A | * | 9/1997 | Ogden et al. .......... 128/205.25 |
| D443,355 S | * | 6/2001 | Gunaratnam et al. ... D24/110.1 |
| 6,374,826 B1 | | 4/2002 | Gunaratnam et al. .. 128/206.27 |
| 6,520,182 B1 | | 2/2003 | Gunaratnam ........... 128/206.27 |
| 6,532,961 B1 | * | 3/2003 | Kwok et al. ........... 128/206.21 |
| 6,691,707 B1 | * | 2/2004 | Gunaratnam et al. .. 128/206.21 |
| 6,712,072 B1 | * | 3/2004 | Lang ...................... 128/206.27 |
| D492,992 S | * | 7/2004 | Guney et al. ........... D24/110.4 |
| 6,789,543 B1 | * | 9/2004 | Cannon .................. 128/207.18 |
| 2004/0045550 A1 | * | 3/2004 | Lang et al. ............. 128/205.25 |
| 2004/0045551 A1 | * | 3/2004 | Eaton et al. ........... 128/206.21 |
| 2004/0112387 A1 | * | 6/2004 | Lang et al. ............. 128/206.24 |
| 2005/0011521 A1 | * | 1/2005 | Sprinkle et al. ........ 128/206.21 |
| 2005/0072428 A1 | * | 4/2005 | Ho et al. ................ 128/205.25 |

FOREIGN PATENT DOCUMENTS

WO     WO 0078384     12/2000

* cited by examiner

*Primary Examiner*—Teena Mitchell
(74) *Attorney, Agent, or Firm*—MacMillan, Sobanski & Todd, LLC

(57) ABSTRACT

A nasal mask for applying pressurized gas to a user's respiratory system. The mask includes an inflatable seal which is at least partially filled with a soft open cell foam. The seal includes a manual pump and a pressure release valve for inflating and deflating the seal. The mask includes an brow bar which is connected through a bridge to the mask body. The bridge can be adjusted to position the brow bar against the user's forehead for supporting an upper portion of the mask. Headgear for attaching the mask to the user is attached to the brow bar and is looped over a prong at a lower portion of the mask for securing the lower portion of the mask to the user. The mask can be easily removed from the patient while leaving the headgear and brow bar attached to the user.

8 Claims, 15 Drawing Sheets

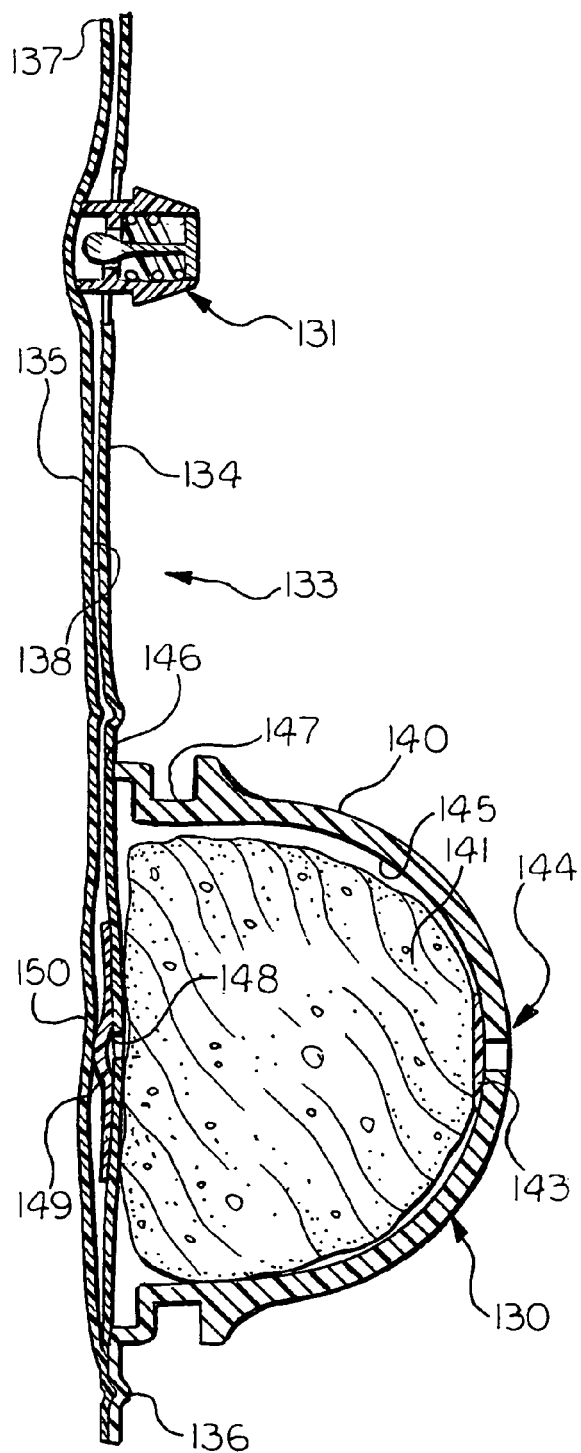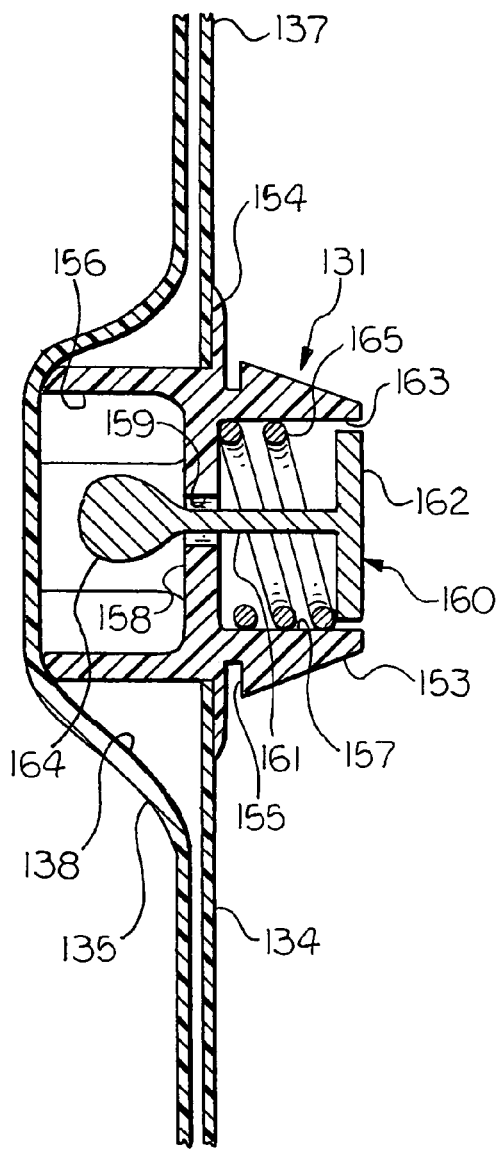
FIG. 25
FIG. 26

ADJUSTABLE NASAL MASK

CROSS-REFERENCE TO RELATED APPLICATIONS

Applicants claim priority to U.S. Provisional Patent Application Ser. No. 60/451,113 filed Feb. 28, 2003.

STATEMENT REGARDING FEDERALLY SPONSORED RESEARCH OR DEVELOPMENT

Not Applicable.

TECHNICAL FIELD

This invention relates to respiratory masks and more particularly to a nasal mask of the type used for applying a continuous or an intermittent positive pressure to a patient's respiratory system for treating illnesses, particularly sleep disorders such as obstructive sleep apnea.

BACKGROUND OF THE INVENTION

Obstructive sleep apnea (OSA) is common sleep disorder suffered by a large number of people. When a person who suffers from OSA has an event, the airway collapses and is blocked, primarily during inspiration. The airway may remain blocked for a few seconds to more than one minute while the person struggles to breath. The person may wake or may move to change his or her sleep position to until the blockage is opened. Severe snoring is frequently a precursor to OSA. During severe snoring, the airflow to the patient's lungs may be restricted, but not totally blocked. One treatment for OSA is the application of a continuous positive airway pressure (CPAP) to the patient's respiratory system. This is most frequently accomplished by the patient wearing a nasal mask during sleep which is connected to a source of pressurized air. When a sufficient air pressure is applied to the nasal mask, the patient's airways become sufficiently inflated and remain open for unrestricted breathing. While evaluating a patient for CPAP treatment, a clinician determines the lowest effective pressure needed for keeping the patient's airway open during sleep.

Various types of CPAP apparatus are well known in the art. The basic CPAP apparatus has a blower which is connected through a pressurized air hose to a nasal mask. The CPAP apparatus is adjusted to provide the lowest effective pressure to the patient for preventing abnormal sleep events. More sophisticated CPAP apparatus includes features such as a ramp delay which applies a reduced pressure to the nasal mask for a period while the patient falls asleep, and then gradually increases the pressure to a programmed level. The CPAP apparatus also may vary the applied pressure to gradually increase the applied pressure in response to sensed sleep events, and to gradually decrease the applied pressure when no sleep events are sensed. In a bi-level form of CPAP apparatus, an effective therapeutic pressure is applied to the nasal mask when the patient begins to inhale and the pressure is reduced when the patient begins to exhale. Bi-level apparatus can increase the comfort of CPAP therapy by reducing the work of exhaling against the therapeutic pressure, particularly for patients who require a high therapeutic pressure.

Some patients do not comply with the prescribed CPAP treatment due to mask discomfort where it contacts the face, especially at the bridge of the nose. There has been significant work by CPAP equipment manufacturers to improve mask comfort, since the mask must be worn whenever the patient is sleeping. To be effective, the mask requires a comfortable seal which will adjust to a wide differences in facial configurations of different patients. The seal also must adjust to facial changes when a user changes sleep positions. A number of different seal configurations have been used in the past. These include flexible membranes which can conform to the face and the bridge of the nose, foam filled seals, inflated seals, and seals filled with a gel type material. Each type of seal has positive and negative features.

The mask is secured to the patient with headgear which typically is in the form of straps which extend around the head. Preferably, the headgear is designed so that it is easily adjusted by the patient and is easily attached to the patient. The patient should be able to remove the mask during the night and to easily reattach the mask, for example, if the patient needs to go to the toilet. However, many mask/headgear configurations are not easy for the patient to attach and remove.

BRIEF SUMMARY OF THE INVENTION

The invention is directed to an improved nasal mask and to an improved headgear arrangement for securing the mask to a patient. Although the nasal mask is described herein for use in CPAP therapy for preventing OSA, it will be appreciated that the mask may be used for other therapy and treatments which require a nasal mask for applying a positive gas pressure to a patient's respiratory system.

One feature of the mask is an inflatable seal having a chamber which is at least partially filled with a soft, open cell foam. The seal includes a manually operated pump and a manually operated, normally closed pressure release valve which are mounted on a mask body and are connected to the seal chamber for adjusting the pressure within the seal. By inflating or deflating the seal, the seal is easily customized for patient comfort and for preventing air leaks between the seal and the patient's face.

Another feature of the mask is an adjustable brow bar or forehead support which can be pivoted relative to the mask shell to limit pressure on the bridge of the patient's nose. An adjustable bridge connects the brow bar to a mask body. The bridge has a pivotal connection to the brow bar. Headgear which attaches the mask to the patient is attached to the brow bar for securing the upper portion of the mask to the patient. The bridge is designed to be easily detached from the brow bar to facilitate removal of the mask from the patient while the brow bar remains attached to the patient. The headgear also includes a lower strap which fits into a recess or over one or more flanges or prongs on a lower portion of the mask shell. If the patient needs to temporarily remove the mask, for example, to go to the toilet or to answer the telephone, the strap is lifted from the recesses or prongs on the lower portion of the mask shell and the adjustable bridge is detached from the brow bar. The headgear and brow bar remain on the patient so that the mask is easily reattached to the patient without requiring reattachment or adjustment of the headgear. It can be difficult for a patient to talk while wearing the mask, since there is a tendency for the pressurized air applied to the nose to flow out the mouth. The patient also may easily lift the strap from the recess and tilt the mask away from the nose, for example, to allow the patient to talk. The lower portion of the mask is easily reattached to continue with the CPAP therapy.

Accordingly, it is an object of the invention to provide an improved nasal mask for applying a positive pressure to a mask user's airway.

Other objects and advantages of the invention will become apparent from the following detailed description of the invention and the accompanying drawings.

BRIEF DESCRIPTION OF THE DRAWINGS

FIG. 25 is a cross sectional view through the pump and the pressure release valve as taken along line 25—25 of FIG. 21;

FIG. 26 is an enlarged cross sectional view through the pressure release valve;

DETAILED DESCRIPTION OF THE INVENTION

Figure 1:
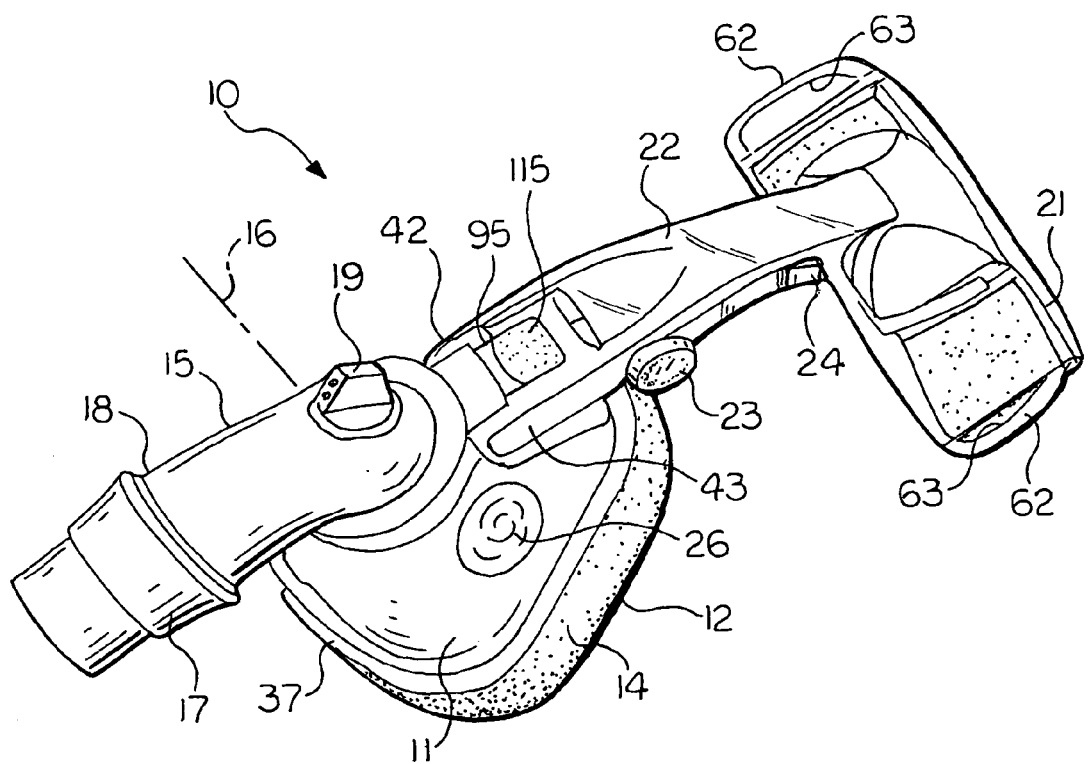
FIG. 1 is a perspective view of a mask according to the invention as seen from the right front side.
Figure 2:
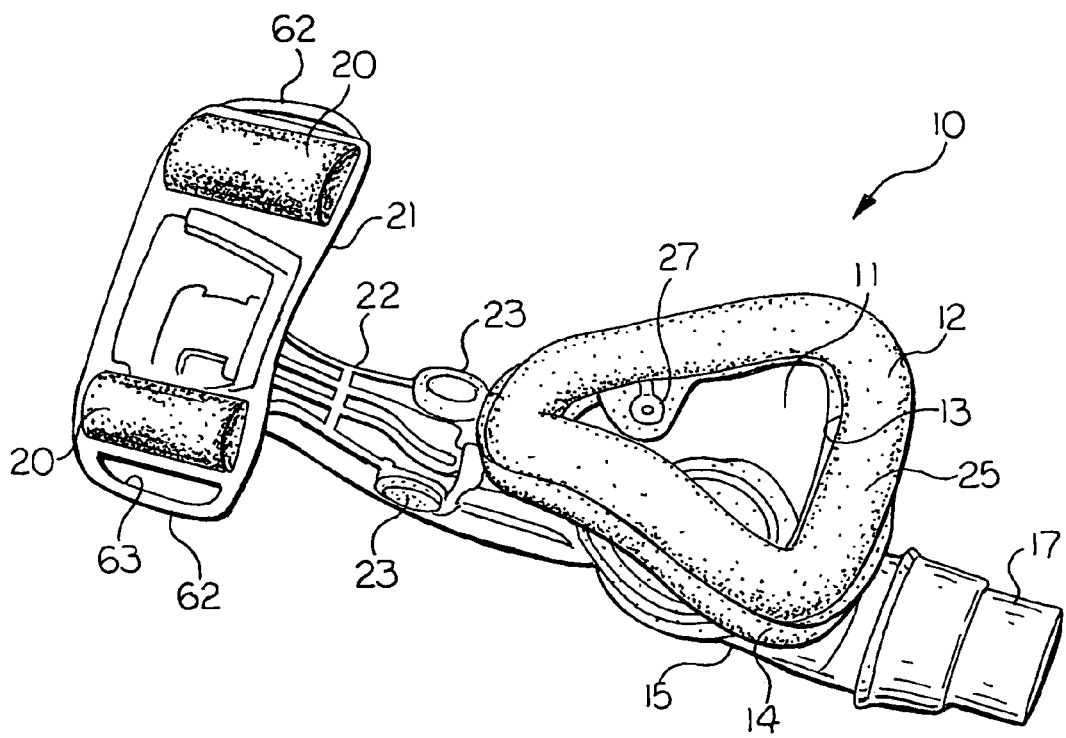
FIG. 2 is a perspective view of the mask of FIG. 1 as seen from the back right side.

Referring to the drawings, FIGS. 1–4 show a nasal mask 10 according to a first embodiment of the invention for applying a positive gas pressure to a patient's respiratory system. The mask 10 is of a type which may be worn by a patient during sleep for treating sleep disorders, such as sleep apnea. The mask 10 is used for applying either a continuous or an intermediate positive air pressure from CPAP apparatus to the patient's respiratory system to prevent soft tissues from collapsing and blocking the passages during breathing, for example, for preventing OSA. However, it will be appreciated that the nasal mask 10 may be used for applying a positive gas pressure to a patient's airway for other medical purposes.

The mask 10 includes a body 11 and a cushion 12 which has a central opening 13 for receiving the patient's nose. Preferably, the cushion 12 is removable from the mask body 11 to facilitate cleaning and replacement. The cushion 12 has a contour which generally conforms to the contour of an average person's face around the nose. A collar 14 is shown for securing the cushion 12 to the mask body 11. However, it should be appreciated that other known mask cushion attachment methods also may be used. An elbow 15 is attached to a front of the body 11 to rotate about an axis 16. A swivel connector 17 is connected to an end 18 of the elbow 15 for attachment to an air hose (not shown) which delivers pressurized air to the patient from conventional CPAP apparatus (not shown).

A vent 19 is shown mounted on the elbow 15. The illustrated vent 19 is of the type described in U.S. Pat. No. 6,435,181. However, the vent 19 does not form a part of the invention and other known types of CPAP mask vents also may be used with the mask 10. It should be understood that the vent 19 may be attached to or may be an integral part of the mask body 11 rather than on the elbow 15, as illustrated.

Many users of CPAP masks have discomfort where the mask presses on the bridge of the user's nose. The headgear which attaches the mask to the patient frequently has a point of attachment to the mask at or adjacent the bridge of the nose. This is necessary to keep the mask sufficiently tight to form a seal between the cushion and the irregular facial surfaces at the bridge of the nose. Excessive pressure on the bridge of the nose can be painful for the user. The discomfort is aggravated by the fact that the mask is typically worn at night for 6 to 8 or more hours. One method for reducing the pressure on the bridge of the nose has been to mount a pad on an extension from the top of the mask body. The pad rests against the patient's forehead to limit the pressure on the bridge of the nose, to help maintain a constant mask seal position relative to the face, and to provide support for the upper portion of the mask 10. However, such a mask requires different configurations for fitting different patients. Masks of this type have been adapted for different patients by using different thickness pads or by providing some form of adjustment in a mounting assembly for the pads. This allows setting the angle of the mask body relative to the bridge of the nose.

According to one feature of the invention, the mask 10 is provided with one or more pads 20 mounted on a brow bar 21. The pads 20 are adapted to rest against the patient's forehead. An adjustable bridge 22 connects between the mask body 11 and the brow bar 21. The illustrated bridge 22 is mounted to rotate on the mask body 11 and is designed to lock in a number of different rotational positions for adjusting to different user facial configurations. The user presses on tabs or buttons 23 on the bridge 22 for releasing the lock between the bridge 22 and the body 11 during adjustment of the angular position of the bridge 22 relative to the body 11. The brow bar 21 is mounted to pivot on the bridge 22 so as to self align with foreheads of different users. The bridge 22 also includes release tabs or buttons 24 which, when squeezed, allows the bridge 22 to be separated from the brow bar 21. The upper portion of the mask 10 can be adjusted for a specific user relative to the user's forehead by positioning the mask over the user's nose in a position wherein the cushion 12 forms a seal around the nose, pressing on the buttons 23 to unlock the bridge 22, rotating the bridge 22 until the brow bar 21 rests against the user's forehead, and releasing the buttons 23 to lock the bridge position.

According to another feature of the invention, the mask 10 is provided with a novel cushion 12 for forming a comfortable seal between the mask 10 and a user's face. The cushion 12 is in the form of a highly flexible tube 25 which is secured to the mask body 11 with the collar 14. The tube 25 may be secured to the collar 14 which in turn is secured to the mask body 11. A pump 26 is attached to the tube 25 for inflating the tube 25, and a pressure release valve 27 is attached to the tube 25 for deflating the tube 25. The pump 26 and the valve 27 are mounted to extend through openings on opposite sides of the mask body 11. Preferably, the tube 25 is at least partially filled with a soft open cell foam which helps press the cushion 12 against the facial surfaces of a mask user when the cushion is uninflated or partially inflated.

Figure 5:
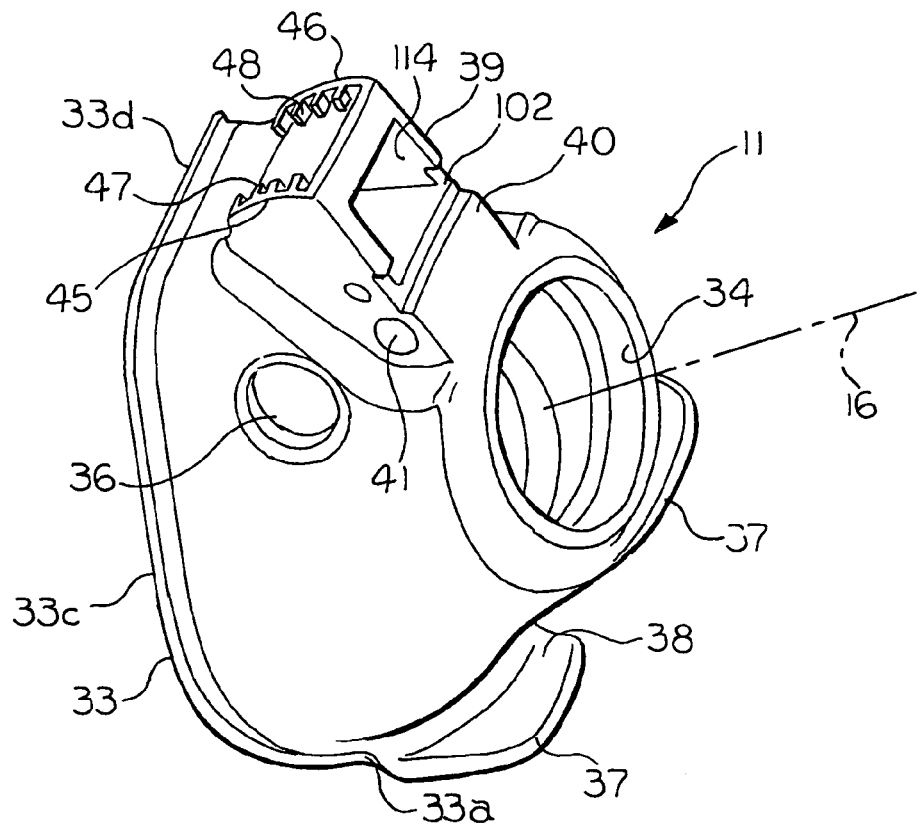
FIG. 5 is a left front perspective view of the mask body.
Figure 6:
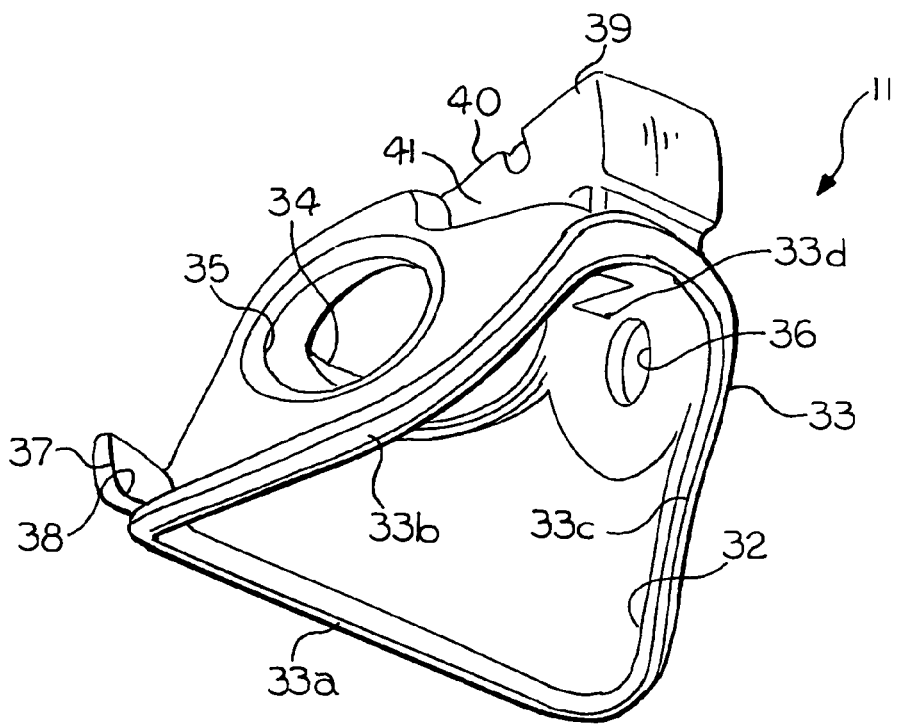
FIG. 6 is a right front rear perspective view of the mask body of FIG. 5.

Referring to FIGS. 5 and 6, details of the mask body or shell 11 are shown. The body 11 has an opening 32 surrounded by a rim 33 which is shaped to substantially conform to an average user's facial configuration surrounding the nose. The cushion 12 accommodates facial variations. Optionally, the mask manufacturer may offer two or more mask shells 11 and cushions 12 of different sizes and shapes to further accommodate different facial configurations. A lower portion 33a of the edge 33 is designed to extend below the user's nose across the upper lip. Side portions 33b and 33c extend generally along the sides of the nose and an upper portion 33d extends over the bridge of the user's nose.

The cushion 12 is designed to be positioned against and to be secured to the rim 33 by the collar 14 which snaps over or otherwise engages the rim 33, as is well known in the art. Opposite the opening 32, the body 11 forms a circular opening 34 in which the elbow 15 is mounted to rotate about the axis 16. An opening 35 is formed through one side of the body 11 for receiving the pump 26 which inflates the cushion 12, and an opening 36 is formed through the opposite side of the body 11 for receiving the release valve 27. The pump 26 may consist of a resilient, semi-spherical bulb which frictionally engages the opening 35 and the release valve 27 may have a generally tubular exterior which frictionally engages the opening 36. The bases of the pump 26 and the release valve 27 may form groves which retain the pump 26 and the release valve 27 on the body 11.

One or more flanges or prongs 37 (two shown) are formed on the body 11 to extends away from the lower portion 33a.

A groove or recess 38 is formed between the flanges 37 and the body 11. An elastic lower headgear strap is positioned in the recess 38 for holding the lower end of the mask 11 against the patient's upper lip, as will be discussed in greater detail below.

Referring to FIGS. 5–9, the mask body 11 also includes a bracket 39 to which the adjustable bridge 22 is attached. The bracket 39 includes a block 40 in which a hole 41 is formed. The bridge 22 has two spaced, parallel extensions 42 and 43. The extensions are resilient and include aligned, inwardly directed pins 44 which are adapted to engage the opening 41 on the block 40. This provides a pivotal connection securing the adjustable bridge 22 to the body 11. At an upper end, the bracket 39 has two spaced, parallel ribs 45 and 46. The ribs 45 and 46 have notched opposing inner surfaces 47 and 48, respectively.

Figure 8:
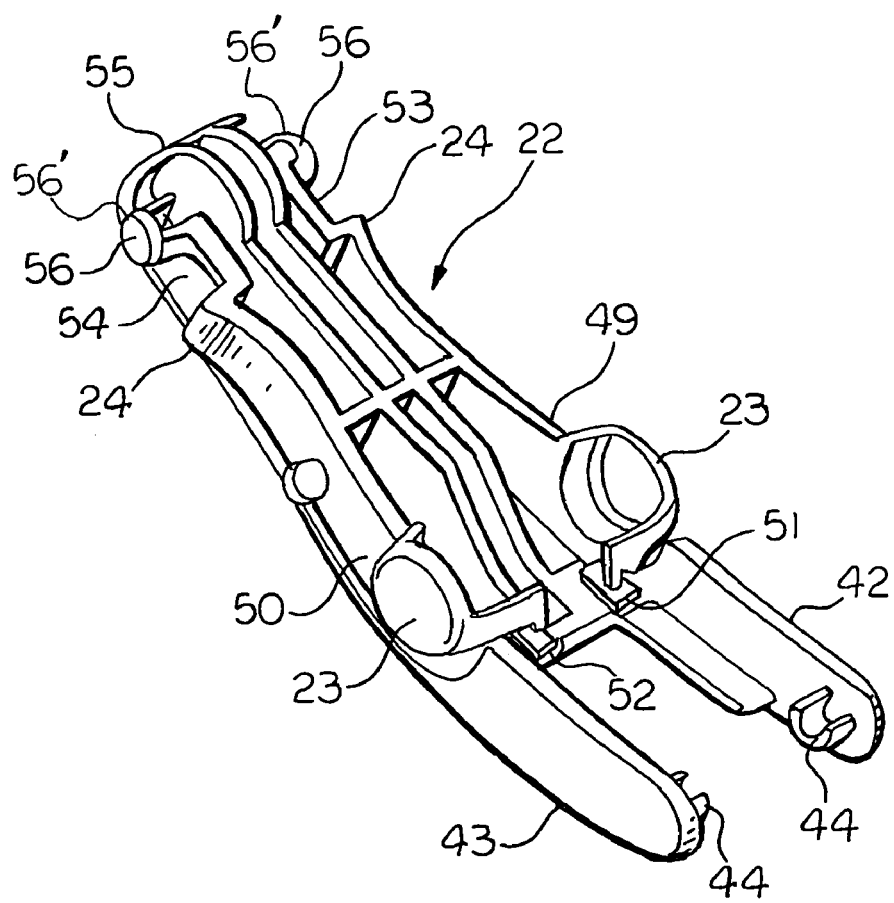
FIG. 8 is a right rear perspective view of the adjustable bridge of FIG. 7.
Figure 9:
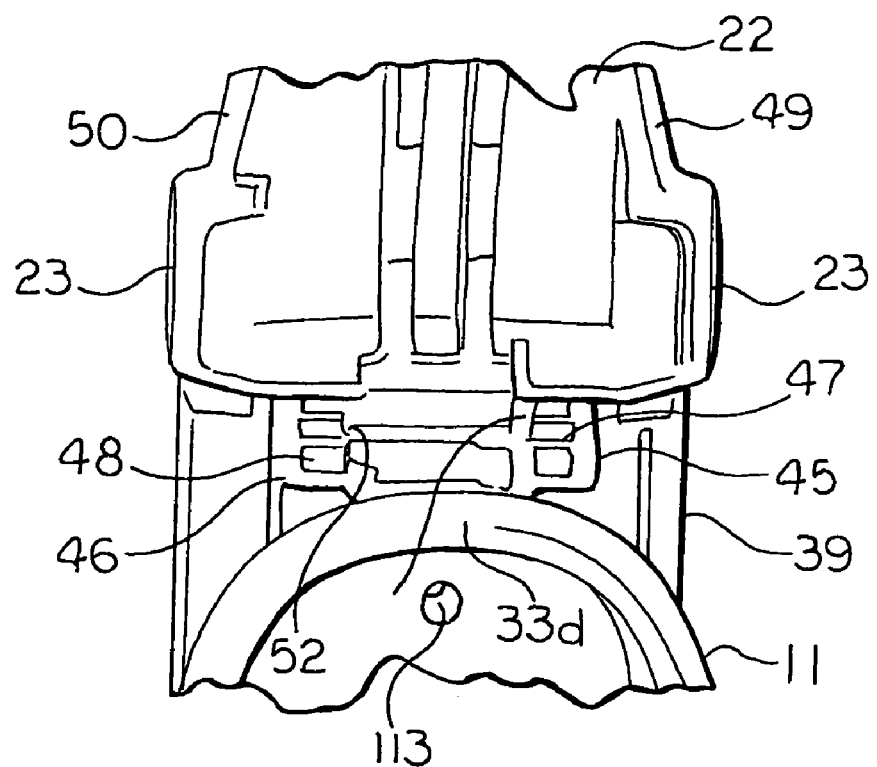
FIG. 9 is an enlarged fragmentary view showing details of the adjustable connection between the adjustable bridge and the mask body.

As best seen in FIG. 8, the bridge 22 has two generally parallel, resilient, cantilevered arms 49 and 50 adjacent the extensions 43 and 44, respectively. Preferably, ends of the arms 49 and 50 are shaped to define the buttons 23. The ends of the arms 49 and 50 also have spaced tabs 51 and 52, respectively. When the bridge 22 is attached to the body 11, the tab 51 engages the notched surface 47 and the tab 52 engages the notched surface 48 to prevent rotation of the bridge 22 relative to the body 11. The angular position of the bridge 22 relative to the body 11 is adjusted by squeezing together the buttons 23 the move the tabs 51 and 52 out of engagement with the notched surfaces 47 and 48. Once the bridge 22 is in a desired position, the buttons 23 are released and the tabs 51 and 52 engage the notched surfaces 47 and 48 on the bracket 39 to lock the angular position of the bridge 22 relative to the body 11.

Figure 7:
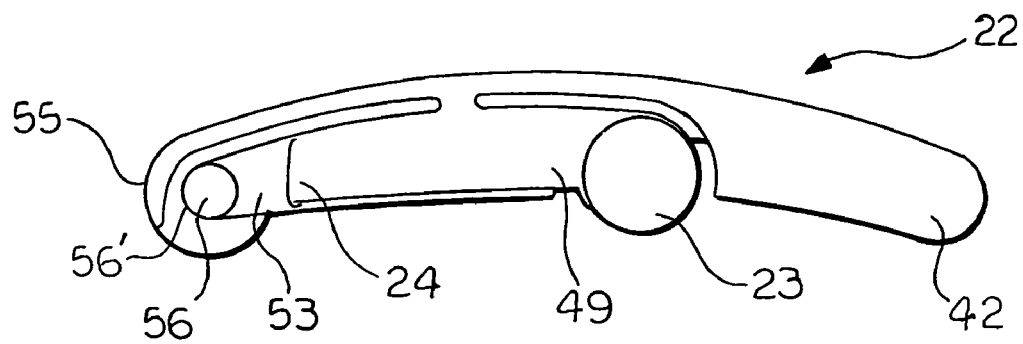
FIG. 7 is a left side elevational view of an adjustable bridge for mounting a brow bar on the mask body.
Figure 10:
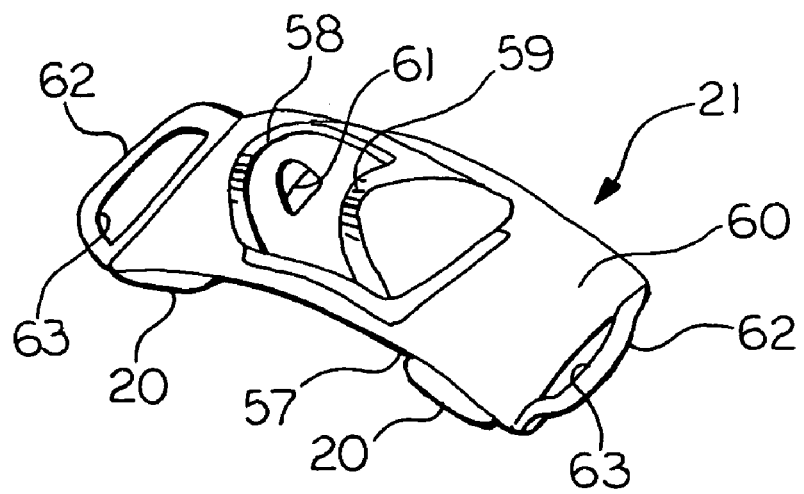
FIG. 10 is a right front perspective view of the brow bar.
Figure 11:
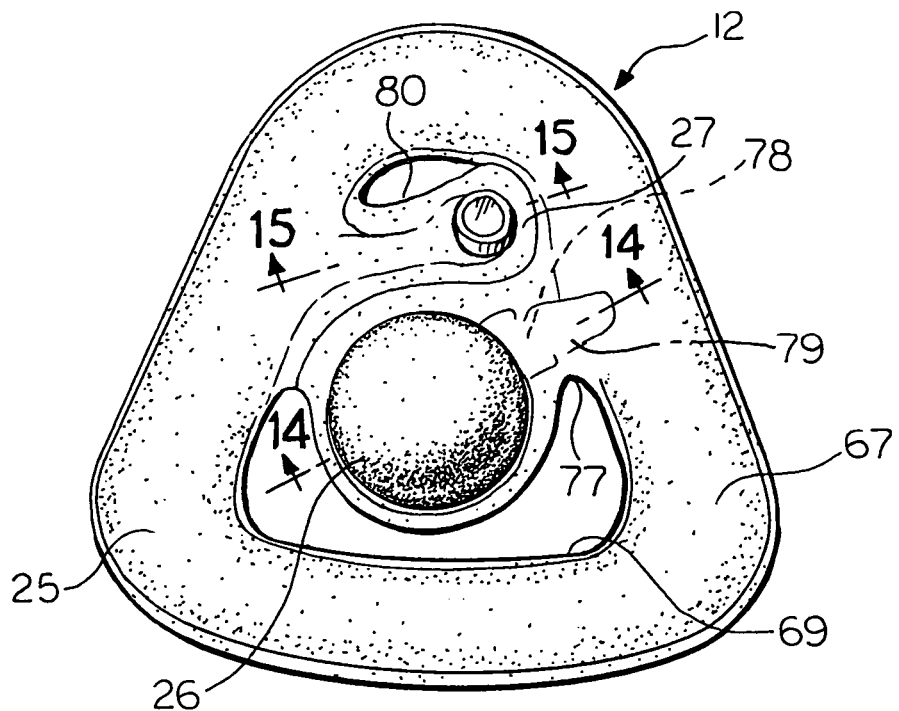
FIG. 11 is a front elevational view of a seal assembly for the mask of FIG. 1.
Figure 12:
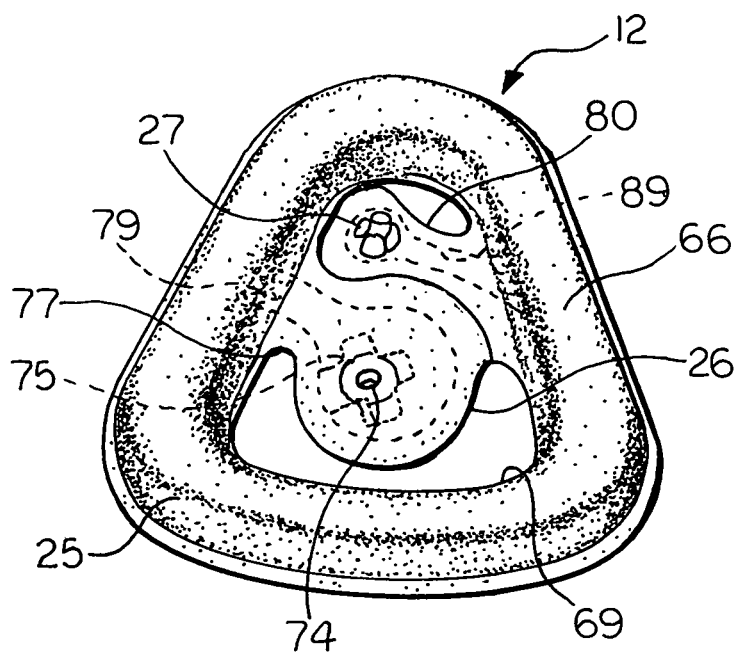
FIG. 12 is rear elevational view of the seal assembly of FIG. 11.
Figure 13:
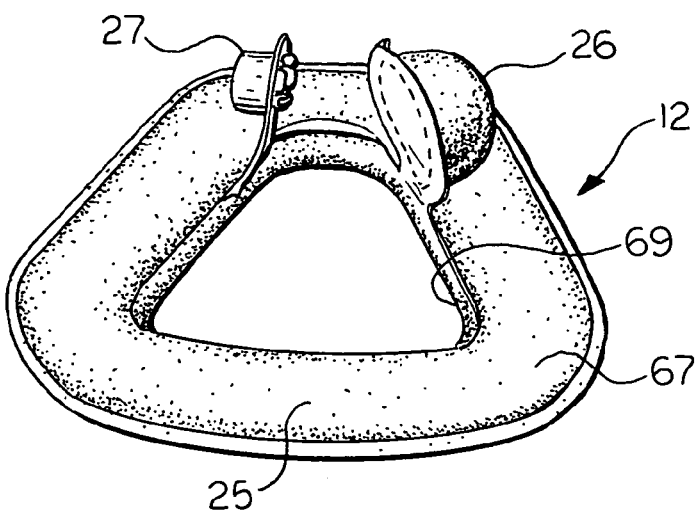
FIG. 13 is lower front perspective view of the seal assembly of FIG. 11, with the pump and release valve shown in position for engaging the mask body.
Figure 14:
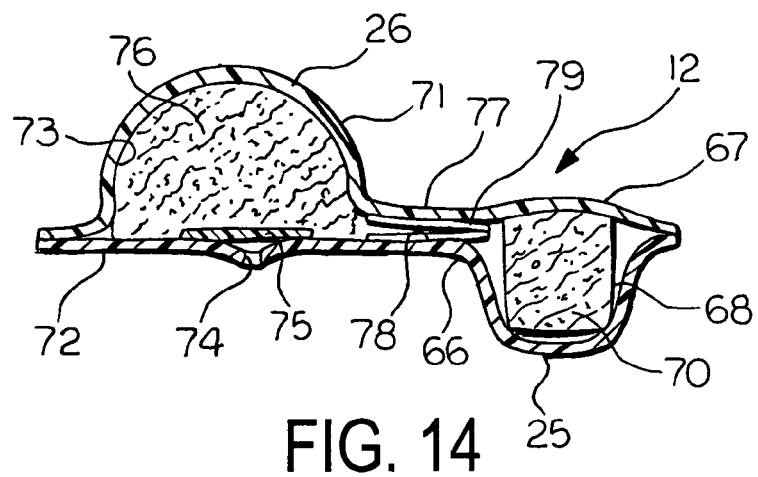
FIG. 14 is a fragmentary cross sectional view as taken along line 14—14 of FIG. 11 showing details of the cushion pump.
Figure 15:
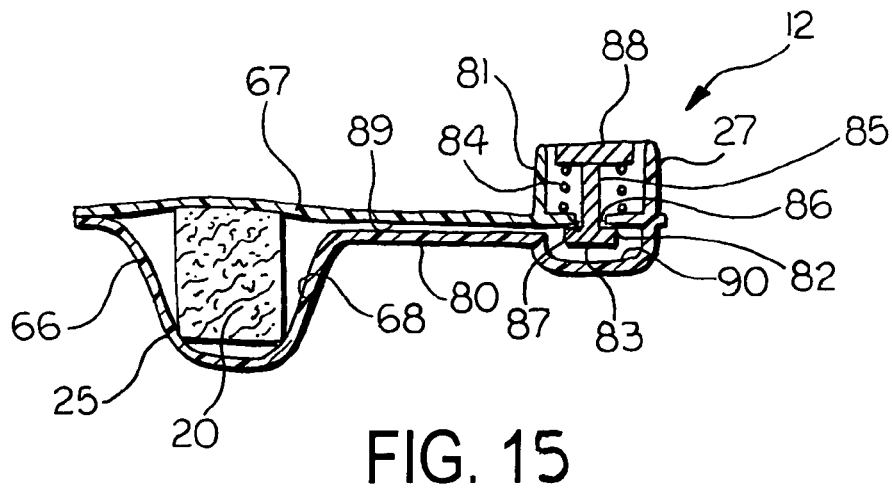
FIG. 15 is a fragmentary cress sectional view as taken along line 15—15 of FIG. 11 showing details of the cushion release valve.
Figure 16:
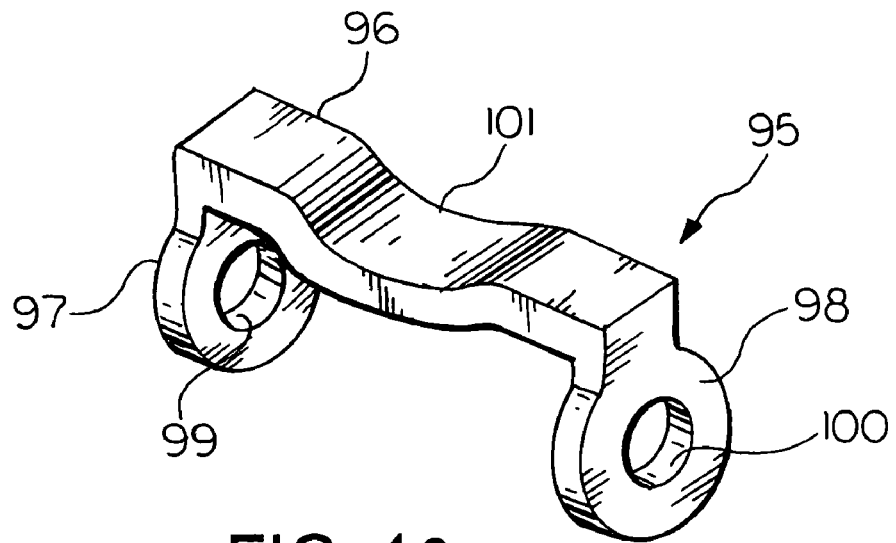
FIG. 16 is an enlarged perspective view of the elbow lock.

FIGS. 7, 8 and 10 show details of the brow bar 21 and of the connection between the brow bar 21 and the bridge 22. The bridge 22 also includes two generally parallel resilient cantilevered arms 53 and 54 which extend towards a brow bar mounting end 55 and which are shaped to define the tabs 24. Axially aligned outwardly directed pins 56 are formed on the arms 53 and 54. The brow bar 21 has a surface 57 on which the pads 20 are mounted, for example, with a suitable adhesive, or with other known methods. The pads 20 are formed from a material which will readily conform to the user's forehead and will be comfortable when the mask 10 is worn for a long period of time. For example, the pads 20 may be gel filled or fluid filled pockets, or of a suitable resilient foam material. If the pad or pads 20 are of a foam material, the surface of the pads 20 which contacts the mask user's forehead may be covered with a soft, comfortable fabric.

The brow bar 21 has two generally parallel spaced flanges 58 and 59 extending above a surface 60. Aligned openings 61 are formed in the flanges 58 and 59 for receiving the pins 56 on the bridge 22. The tabs 24 on the bridge 22 may be squeezed together to permit insertion of the pins 56 into the openings 61 and released to connect the brow bar 21 to the bridge 22, while permitting the brow bar 21 limited rotation relative to the bridge 22. Preferably, ends 56' of the pins 56 are angled inwardly towards the bridge end 55. The angled ends 56' act as cams to deflect the pins 56 towards each other to allow the bridge end 55 to be easily pushed into the space between the flanges 58 and 59 until the pins 56 engage the openings 61 without having to depress the tabs 24. Thus the bridge 22 is easily attached to the brow bar 21 after the brow bar 21 and the headgear are secured to the user. The brow bar 21 also has opposed upturned ends 62, each of which has a slot 63 for attachment to headgear, as will be discussed in greater detail below.

FIGS. 11–15 show details of the cushion 12 with the integral pump 26 and pressure release valve 27. The cushion 12 is mainly formed from two sheets 66 and 67 of a suitable plastic material which can be vacuum formed or otherwise shaped to provide a desired shape. The sheet 66 is sufficiently thin and flexible to readily conform to the mask user's facial surfaces around the nose. The sheet 66 is formed to define a continuous recess 68 which defines a central opening 69 which receives the user's nose. A similarly shaped piece of soft, open cell foam 70 at least partially fills the recess 68. The sheet 67 is positioned over the sheet 66 and the sheets 66 and 67 are sealed together around both sides of the recess 68 to form the inflatable facial seal tube 25. The foam 70 is resilient and helps press the surface of the sheet 66 into facial crevices to maintain a seal between the mask 10 and the user's face when the seal tube 25 is deflated or only partially inflated. The foam 70 provides a baseline support and facial seal, while the inflation provides the extra or "topping" seal effect to customize the seal to the user's face. Without the foam 70, a partially inflated seal could develop deflated areas which do not adequately seal to the user's face. The sheet 67 may be generally flat and heavier than the sheet 66 to provide a surface which abuts the mask body 11 when the seal 12 is attached with the collar 14.

The pump 26 is formed between the sheets 66 and 67 to extend into the seal nose opening 69. The pump 26 includes a bulbous portion 71 formed in the sheet 67. The sheet 66 forms a generally flat bottom 72 to the pump 26. The bulbous portion 71 may be reinforced with a sufficiently resilient material to help the bulbous portion 71 to regain its original shape after it is pressed and released. The space between the bulbous portion 71 and the sheet 66 forms a pump chamber 73. A reinforced air inlet port 74 is formed through the bottom 72. A generally flat resilient valve member 75 is positioned over the port 74. The pump chamber 73 is filled with a resilient open cell material 76 which urges the bulbous portion 71 to its normal shape and also urges the valve member 75 to close the port 74, forming an inlet check valve. The sheets 66 and 67 include an extended portion 77 which forms a passageway 78 connecting the pump chamber 73 to the tube 25. A check valve 79 is located in the passageway 78 to limit air flow only to the direction from the pump chamber 73 to the tube 25. Consequently, when the bulbous portion 71 is depressed, air is forced from the chamber 73 through the passageway 78 and the check valve 79 into the tube 25. When the bulbous portion 71 is subsequently released, air is drawn through the port 74, past the valve member 75 and into the pump chamber 73 as the bulbous portion 71 returns to its normal position. When the cushion 12 is attached to the mask body 11, the extended portion 77 is bent to allow insertion of the bulbous portion 71 of the pump 26 into the mask body opening 35.

The pressure release valve 27 also is connected to an extended portion 80 of the sheets 66 and 67 which extends into the seal nose opening 69. When the cushion 12 is attached to the mask body 11, the extended portion 80 is bent to allow insertion of the release valve 27 into the mask body opening 36. The release valve 27 generally includes a tubular body 81, a valve seat 82 formed within the body 81, a valve member 83 and a spring 84. The valve member 83 has a shank 85 which extends through an opening 86 in the valve seat 82, an enlarged end 87 on the stem 85 which normally closes the opening 86, and an enlarged end which forms a valve operating button 88. The button 88 is adapted to be pushed to open the release valve 27. The spring 84 is compressed between the valve operating button 88 and the valve seat 82 to normally urge the valve member end 87 against the seat 82 to cover the opening 86. The portion 80 of the sheets 66 and 67 forms a passage 89 which connects the tube 25 with a chamber 90 in the release valve 27. When the valve operating button 88 is manually pushed, the end 87 separates from the seat 82, allowing air to vent from the tube 25 through the passage 80, the chamber 90 between the valve stem 85 and the opening 86 and between the valve operating button 88 and the valve body 81.

As previously indicated, pressurized air flows from a supply hose (not shown) through the swivel connector 17 and the elbow 15 into the mask body 11. Normally, the elbow 15 is free to rotate on the mask body 11 about an axis 16. For some applications, it is desirable to use headgear for attaching the mask 10 to the patient which holds the air supply hose to extend above the mask 10 and over the top of the user's head. In this application, it may be desirable to lock the elbow 15 in a position where it is directed upwardly generally parallel to the bridge 22.

Figure 3:
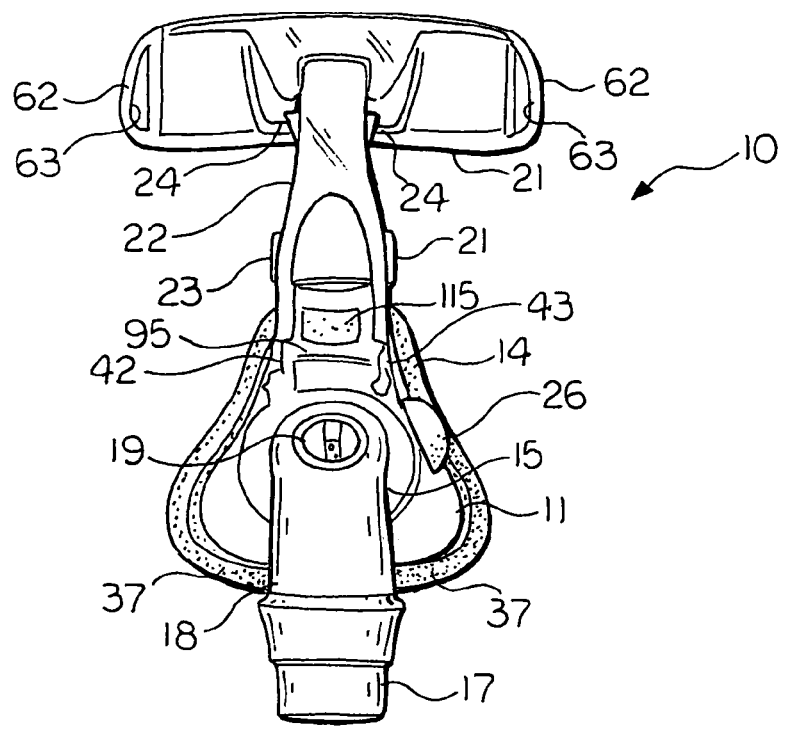
FIG. 3 is a front elevational view of the mask of FIG. 1.
Figure 4:
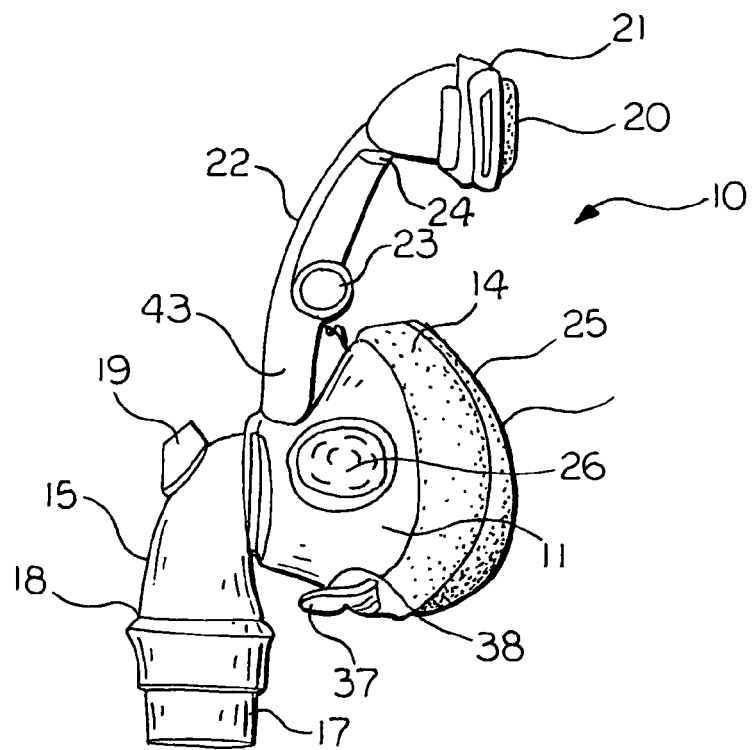
FIG. 4 is a right side elevational view of the mask of FIG. 1.
Figure 17:
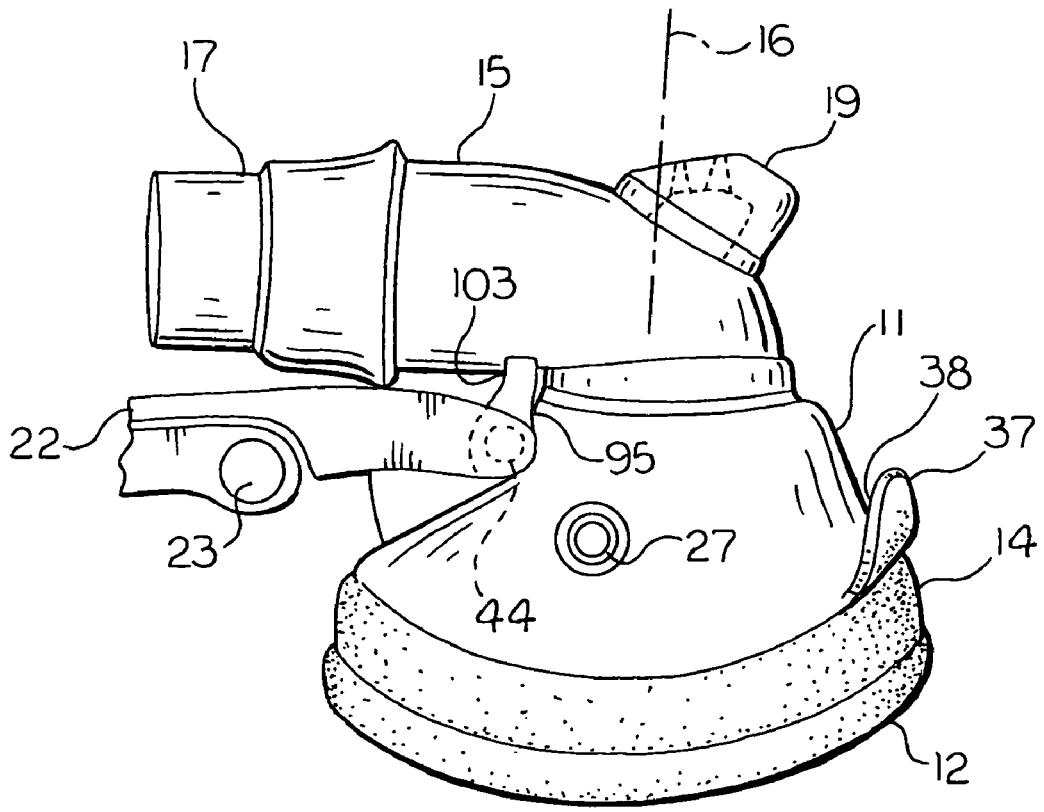
FIG. 17 is a fragmentary perspective view of the mask showing the elbow lock securing the elbow to extend towards the top of the mask.

As best seen in FIGS. 1, 3, 16 and 17, an elbow lock 95 is mounted on the body 11 to rotate between an unlocked position as shown in FIGS. 1, 3 and 4, and a locked position as shown in FIG. 17. The lock 95 has an elongated cross member 96 with perpendicular extensions 97 and 98 from opposite ends. Aligned holes 99 and 100 are formed in the extensions 97 and 98, respectively. The extensions are spaced apart for fitting between the extensions 42 and 43 on the bridge 22 and the holes 99 and 100 are sized to pass the pins 44. The pins 44 secure the lock 95 to the mask body 11 while permitting the lock 95 to rotate on the pins 44. The cross member 96 has a curved upper surface 101 which is adapted to engaged the curved exterior of the elbow 15 when the elbow 15 is locked in the position shown in FIG. 17. When the elbow lock 95 is in the unlocked position, the cross member 95 will be located in a recess 102 (FIG. 5) in the body bracket 39 and the elbow 15 is free to rotate relative to the mask body 11 about the axis 16. The elbow 15 is locked by moving to the upward position as shown in FIG. 17 and rotating the lock 95 to the position shown in FIG. 17. A raised boss 103 on the elbow 15 retains the lock 95 in the locked position.

Figure 18:
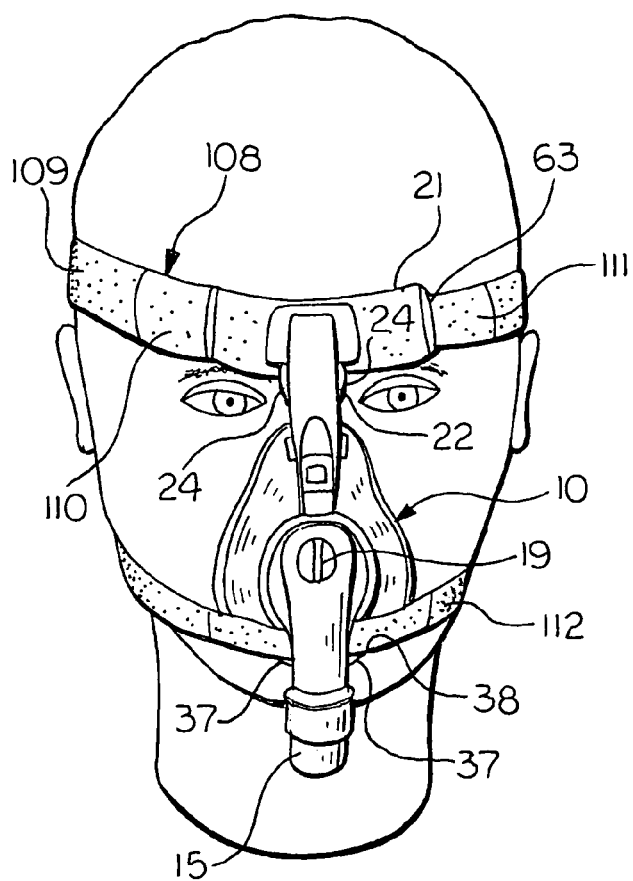
FIG. 18 is a fragmentary perspective view showing the mask of FIG. 1 attached to a patient with headgear.
Figure 19:
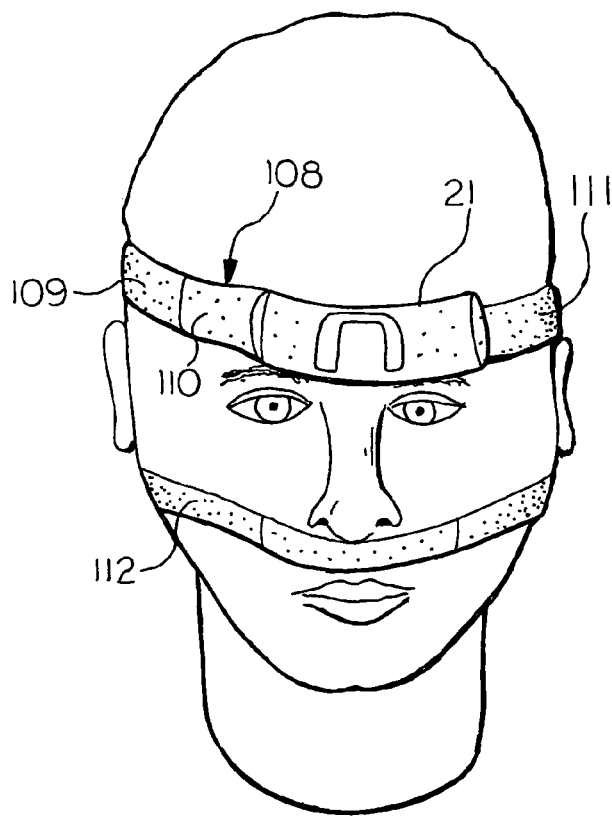
FIG. 19 is a fragmentary perspective view of the patient of FIG. 14 showing the headgear and brow bar attached to the patient, but with the mask removed.
Figure 21:
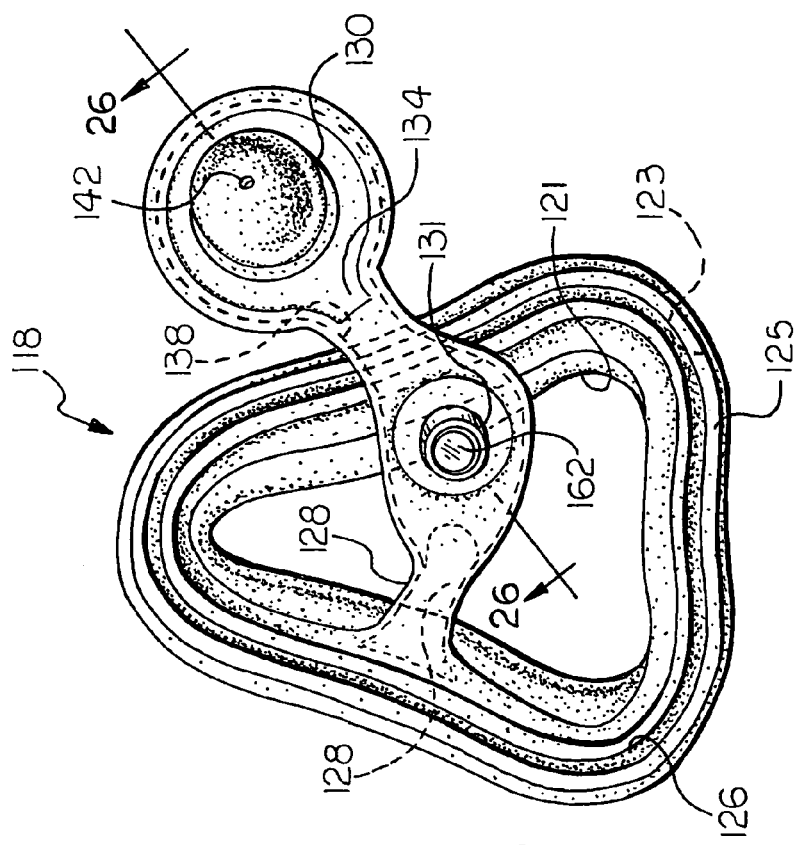
FIG. 21 is a front elevational view of the seal assembly of FIG. 20.
Figure 20:
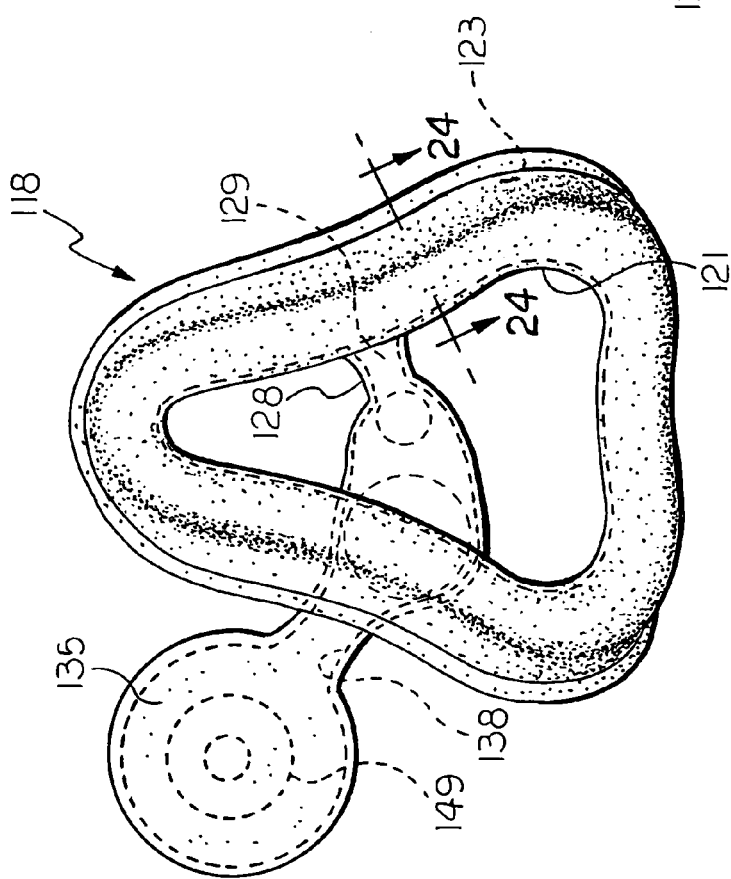
FIG. 20 is a rear elevational view of a modified cushion assembly for a mask according to the invention.
Figure 23:
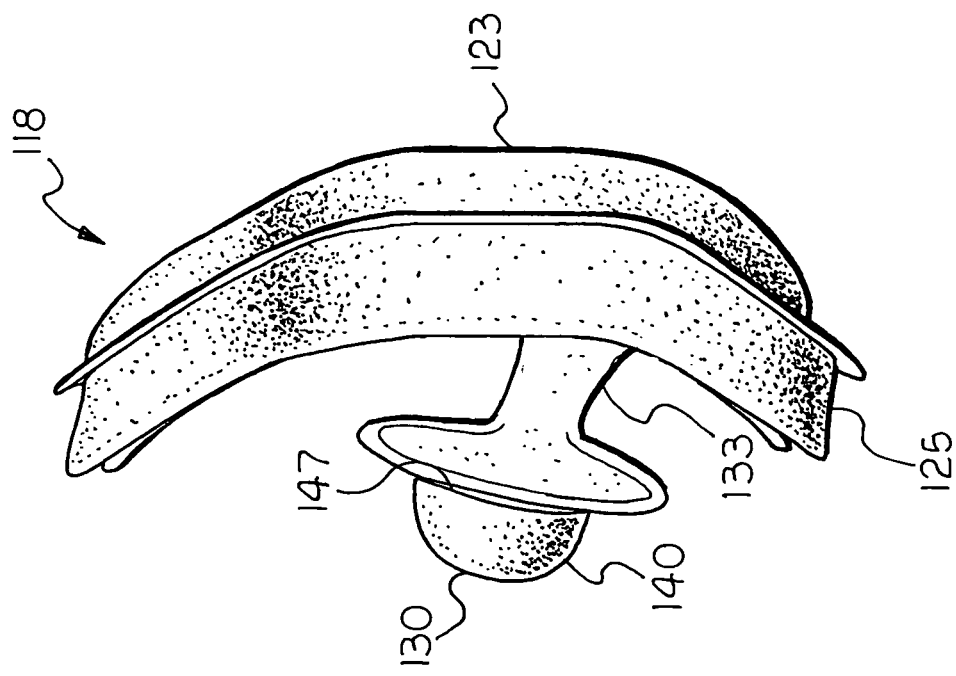
FIG. 23 is a right side elevational view of the cushion assembly of FIG. 20.
Figure 22:
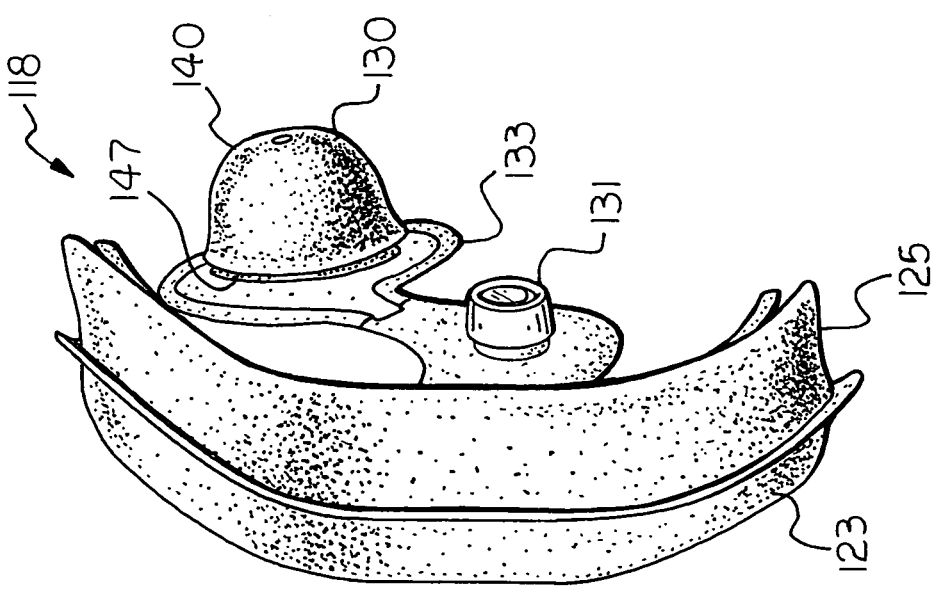
FIG. 22 is a left side elevational view of the cushion assembly of FIG. 20.
Figure 24:
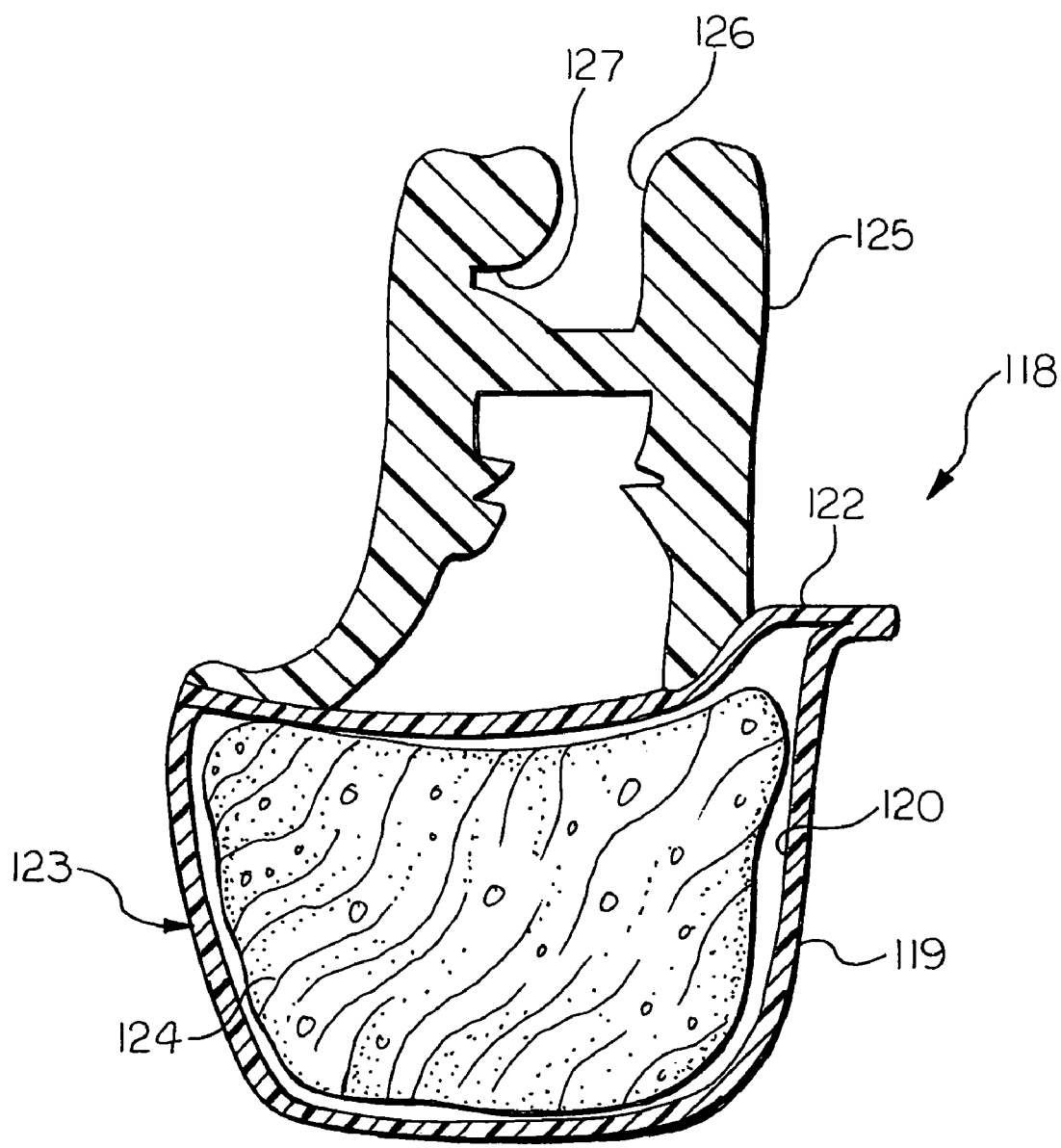
FIG. 24 is a cross sectional view as taken along line 24—24 of FIG. 20.

FIGS. 18 and 19 illustrate securing the mask 10 to a user with headgear 108. The headgear 108 includes an upper strap 109 having two ends 110 and 111 which are attached to the brow bar 21. As is known in the art, the headgear ends 110 and 111 may be provided with hoop and look fasteners, such as Velcro fasteners. The ends 110 and 111 are passed through the slots 63 (FIG. 10) on the brow bar 21, adjusted for the size of the user's head, and secured with the hook and loop fasteners. The headgear 108 also includes a lower strap 112 which also has a length which can be adjusted with hook and loop fasteners. The lower strap 112 is positioned in the recess 38 between the flanges or prongs 37 and the mask body 11 to attach the lower end of the mask 10 to the user. The straps 109 and 112 are elastic to provide sufficient tension to maintain a seal between the mask 10 and the user.

The mask 10 can be removed from a user while leaving the headgear 108 attached by lifting the lower strap 112 out of the recess 38 and squeezing the release tabs 24 to separate the bridge 22 from the brow bar 21. FIG. 19 shows the headgear 108 and the brow bar 21 attached to the user's head with the mask 10 removed. This leaves the user disconnected from the CPAP apparatus and free to get out of bed. When the user returns to bed, it is a simple matter to reattach the bridge 22 to the brow bar 21 and to lift the lower headgear strap 112 into the recess 38. No other mask or headgear adjustments are required when reattaching the mask 10. Since the mask 10 can be removed from the user without removing or changing the position of the headgear 108 on the user, a facial seal is obtained when the mask is reattached to the headgear without having to reposition the headgear.

Referring now to FIGS. 1, 3, 5 and 9, the mask 10 also may include an auxiliary gas inlet 113 (FIG. 9) which, when needed, can be connected to a source of supplemental oxygen. The auxiliary gas inlet 113 is connected to a conventional nipple (not shown) which is located in a recess 114 (FIG. 5) in the bracket 39. When the auxiliary gas inlet 113 is not needed, the recess 114 is closed by a cap 115, as shown in FIGS. 1 and 3. Since the gas inlet 113 communicated directly with the interior of the mask body 11, it will be appreciated that the gas inlet 113 also may be connected to a pressure sensor for monitoring mask pressure during use.

FIGS. 20–26 show details of a modified embodiment of a cushion 118 for the mask 10. The cushion includes a soft flexible sheet 119 of plastic material which is vacuum formed or otherwise shaped to define a recess 120 which extends around a nose receiving opening 121. The recess 120 is closed by a second sheet 122 of plastic material to form an inflatable and deflatable tube 123. The sheet 122 may be somewhat heavier than the sheet 119. Alternately, the sheets 119 and 122 may be replaced with a single sheet of soft flexible plastic material in which the tube 123 is formed and the sheet is folded over to close the tube 123. Preferably, the portions of the cushion which contact a mask user's face are made from plastic materials of a type which are commonly used in nasal masks. These materials are soft, flexible, resistant to facial oil faces and non-allergenic.

Before securing the sheet 122 to the sheet 119, a ring of open cell resilient foam 124 is placed in the recess 120. The sheet 122 is then secured to a collar 125. The collar 125 is releasably attached to the above described mask shell or body 11 via a groove 126 which frictionally engages the shell rim 33 around the opening 32 (FIG. 6.). The groove 126 may have an enlarged portion 127 which receives the mask body rim 33 to retain the cushion 118 on the mask body 11. It will be appreciated that other techniques may be used for attaching the inflatable tube 123 to extend around the mask shell rim 33.

The sheets 119 and 122 have an extended portion 128 which extends into the nose opening 121 and forms a passage 129 which communicates with the interior of the tube 123. A pump 130 for inflating the tube 123 and a pressure release valve 131 for deflating the tube 123 are formed as a unit 133 (FIG. 25) which is connected to the extended portion 128. The unit 133 includes two sheets of flexible plastic 134 and 135 which are connected together along their edges 136, except at an end 137, to form a chamber 138. The end 137 is attached to the extension 128 so that the passage 129 communicates with the chamber 138. The unit 133 is configured and is attached to the extension 128 so that the release valve 131 and the pump 130 can be inserted into openings 36 and 35 (FIG. 6), respectively, in the mask body 11.

As shown in FIG. 25, the pump 130 includes a resilient dome 140 which is filled with a resilient, open cell foam 141. The dome 140 has an air inlet opening 142. The foam 141 presses a resilient disk 143 over an interior side of the opening 142 to form an air inlet check valve 144. When the dome 140 is released after being depressed, air is drawn through the opening 142 and past the disk 143 into an interior 145 of the dome 140 as the dome 140 expands to its original shape. The dome 140 has a perimeter 146 which is attached to the sheet 134. An annular groove 147 is formed in the dome 140 adjacent to the perimeter 146 for engaging the mask body 11 when the dome 140 is inserted into the mask body opening 35 (FIG. 6). An air outlet opening 148 connects the dome interior 145 with the chamber 138. A resilient disk 149 located in the chamber 138 is pressed over the opening 148 to form an outlet check valve 150. When the dome 240 is depressed, air in the interior 145 is forced through the opening 148, past the check valve 150, through the chamber 138 and the passage 129 into the inflatable tube 123.

FIGS. 25 and 26 show details of the release valve 131 which vents air from the inflatable tube 123. The valve 131 has a housing 153 which is formed from a resilient material, such as a resilient rubber or plastic material. The housing 153 has a flange 154 which is bonded or fused to the sheet 134. An annular groove 155 is formed to extend around the housing 153 adjacent the flange 154. When the release valve 131 is inserted into the mask body opening 36 (FIG. 5), the perimeter of the opening 36 extends into the groove 155 to retain the release valve 131 in the opening 36.

The valve housing 153 has an interior portion 156 which is located in the chamber 138 and a tubular exterior portion 157 which is open to atmosphere. A web 158 separates the interior portion 156 from the exterior portion 158. An opening 159 extends through the center of the web 158. A valve member 160 is positioned in the housing 153. The valve member 160 has a shank 161 which extends through the opening 159. The shank 161 has a smaller diameter than the opening 159 so that air can flow between the shank 161 and the wall of the opening 159. The valve member 160 has a valve operating button 162 located on an exterior end of the shanks 161. A gap 163 is formed between the button 162 and the valve housing 153. The shank 161 has a bulbous portion 164 which is located on an interior side of the web 158. The bulbous portion 164 is sized and shaped to block the opening 159 when in contact with the web 158. A compression spring 165 is positioned between the valve operating button 162 and the web 158 to urge the bulbous portion 164 against the web 158 to close the valve 131. When the button 162 is pushed, air from the inflatable tube 123 is vented through the passage 129, the chamber 138 and the valve 131 to atmosphere.

When the mask is first used by a patient, the pump 130 and the pressure release valve 131 are used to increase and decrease the inflation of the tube 123 until the patient finds the most comfortable and effective facial seal. The inflation of the tube 123 may not need future adjustment, unless the patient experiences some discomfort from the mask pressure.

Figure 27:
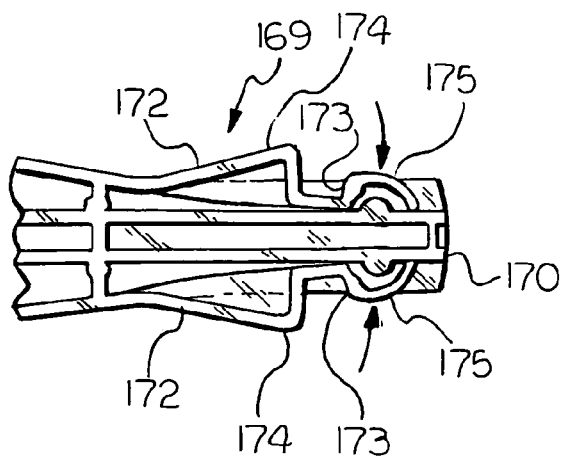
FIG. 27 is an enlarged fragmentary bottom elevational view through a modified bridge for a mask according to the invention showing details of the end which attaches to the brow bar.
Figure 28:
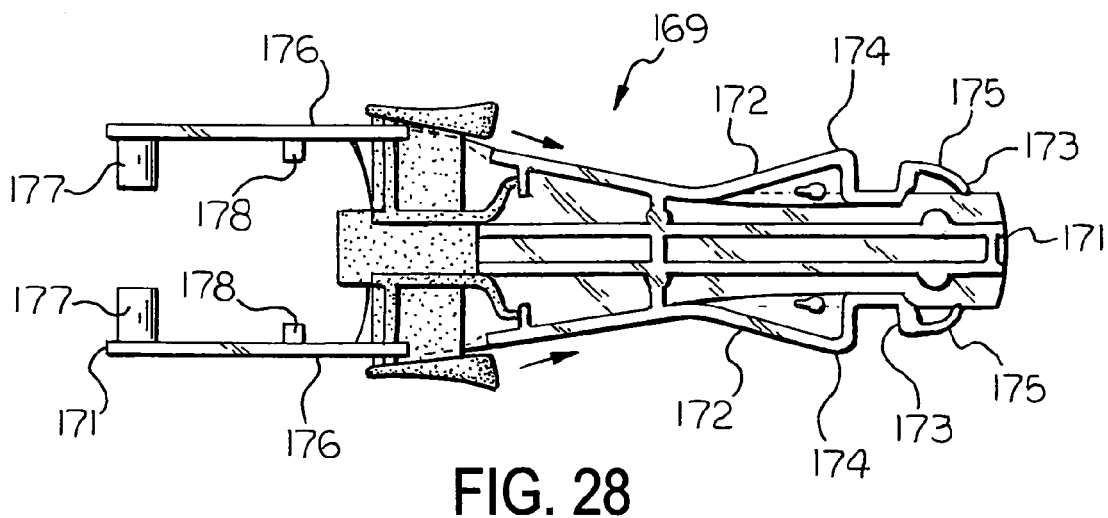
FIG. 28 is an enlarged bottom view of the bridge of FIG. 27.
Figure 29:
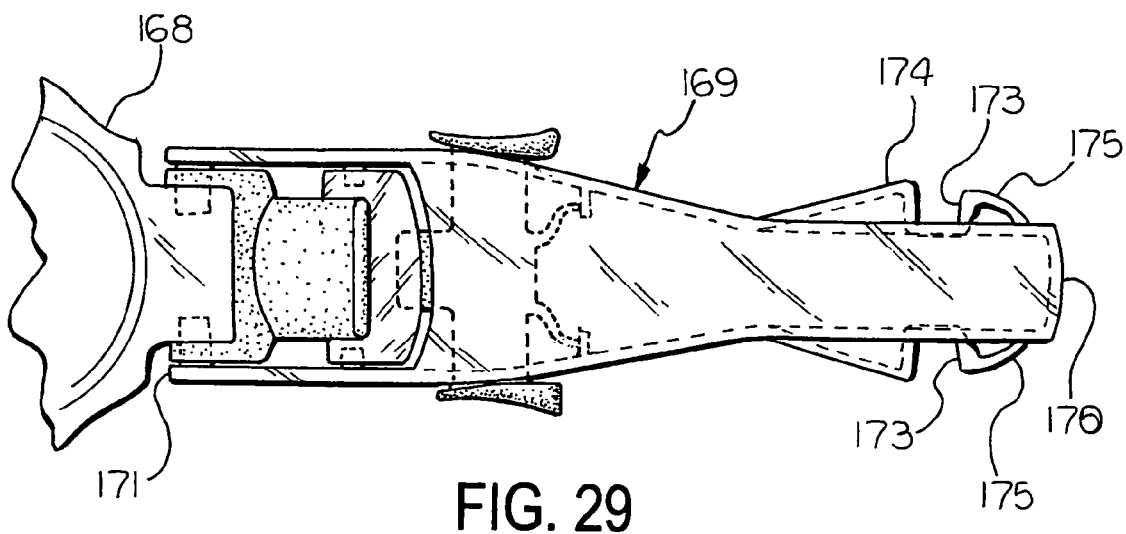
FIG. 29 is a fragmentary top plan view showing details of the connection of the bridge of FIG. 27 to the mask shell.

FIGS. 27–31 show a modified structure for connecting the brow bar 21 to a mask body 168. The structure includes a modified bridge 169 which has an end 170 which is releasably connected to the brow bar 21 and an end 171 which is attached to the mask body 168. The bridge 169 is molded from a resilient plastic material. The bridge 169 has a pair of spaced resilient arms 172 which project towards the end 170. Axially aligned pins 173 project outwardly from adjacent free ends of the arms 172 for engaging the aligned openings 61 (FIG. 10) on the brow bar 21. Each arm 172 has a knob or tab 174 for use in disengaging the bridge 169 from the brow bar 21 by squeezing the tabs 174 together. Preferably, ends 175 of the pins 173 are angled or curved towards the bridge end 170 to act as cam surfaces which will push the pins 173 towards each other as shown in FIG. 27, bending the arms 170, as the bridge 169 is pushed into the brow bar 21. This allows easy attachment of the mask to the brow bar without the need to squeeze the tabs 174. The connection between the bridge end 170 and the brow bar 21 permits limited rotational movement of the brow bar 21 relative to the bridge 169. This allows the brow bar 21 to self align with a mask user's forehead for different forehead shapes.

It will be appreciated that the bridge end 170 may be modified so that the aligned pins 173 project inwardly towards each other and that the brow bar can be provided with a single opening (not shown) having opposed ends which are engaged by the pins to releasably connect the bridge to the brow bar while permitting the brow bar to rotate on the pins to align with a mask user's forehead.

The bridge 169 has a pair of spaced parallel resilient arms 176 extending to the end 171. A pair of aligned pins 177 project from free ends of the arms 176 towards one another adjacent the bridge end 171. A second pair of aligned pins 178 project towards one another from an intermediate location on the arms 176. A lock member 179 is mounted on the bridge 169 for locking the position of the bridge 169 relative to the mask body 168. The lock member 179 is mounted on the bridge 169 for limited movement in a generally longitudinal direction along the bridge 169. Two resilient fingers 180 on the lock member 179 engage tabs 181 on the bridge 169. The tabs 181 act as springs urging an end 182 of the lock member 179 towards the bridge end 171. The lock member 179 also included opposed knobs 183. The knobs 183 can be grasped by a mask user to manually move the lock member 179 a short distance towards the bridge end 170 against the force of the resilient fingers 180, moving the lock member end 182 away from the bridge end 171.

Figure 30:
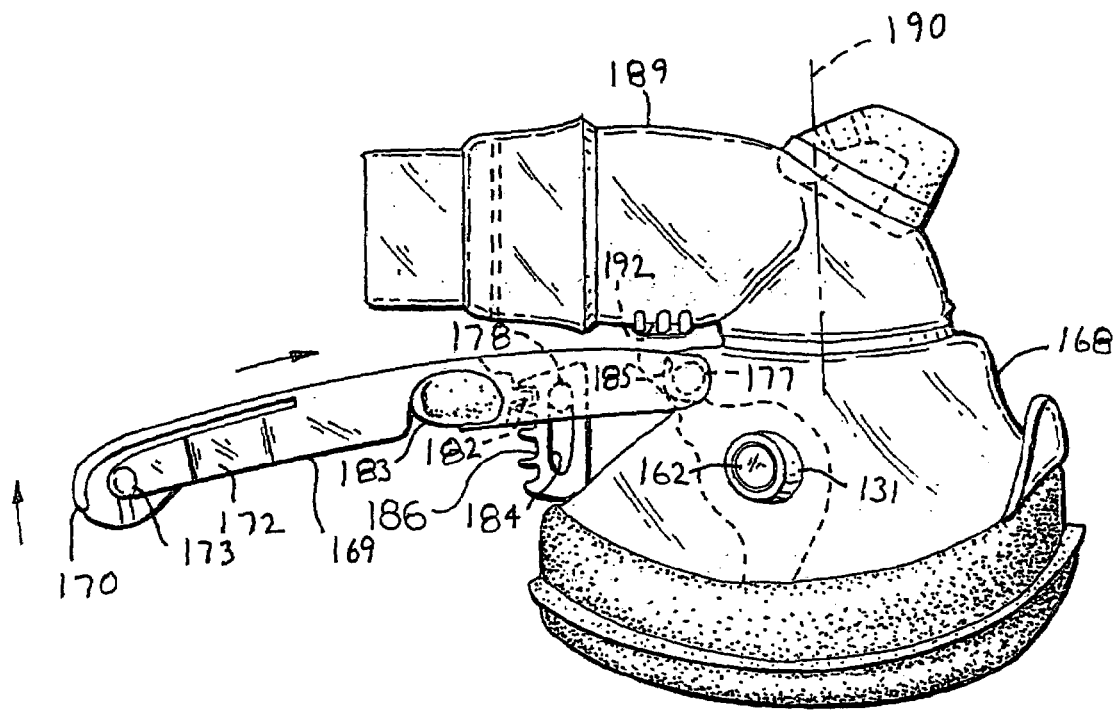
FIG. 30 is a side elevational view of the mask showing details of the connection of between the bridge and the mask shell, with the bridge shown in its uppermost position.
Figure 31:
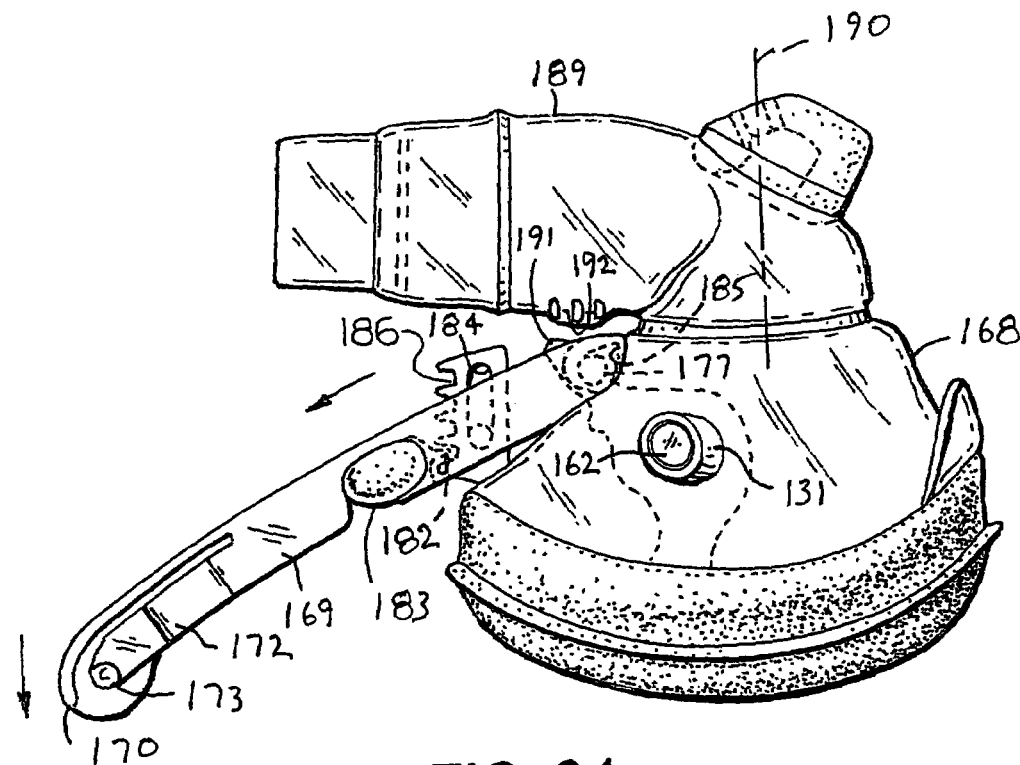
FIG. 31 is a side elevational view similar to FIG. 30, but with the bridge shown in its lowermost position.

FIGS. 30 and 31 show the bridge 169 attached to the modified mask body 168. The pairs of pins 177 engaging laterally spaced parallel slots 184 in the mask body 168 and the pins 178 laterally engaging spaced parallel slots 185 in the mask body 168. The slots 184 and 185 are arranged at an angle relative to each other, preferably with the slots 184 generally perpendicular to the face of a mask user and the slots 185 generally parallel to the face of a mask user. As a consequence of having an angular relationship between the slots 184 and 185, the angle of the bridge 169 is adjustable relative to the mask body 168.

The bridge 169 is shown in its furthest upper position in FIG. 30 and in its furthest lower position in FIG. 31. When the bridge 169 is moved from the position of FIG. 30 to the position of FIG. 31, the pins 177 move down in the slots 185 and the pins 178 move to the left in the slots 185. Alternately, when the bridge 169 is moved from the position of FIG. 31 to the position of FIG. 30, the pins 177 move up in the slots 184 and the pins 178 move to the right in the slots 185. Thus, the bridge 169 does not pivot about an axis as it is adjusted. The position of the bridge 169 is adjusted to accommodate the configuration of a mask user's nose bridge and forehead in order to obtain the best facial seal at the nose bridge without placing excess pressure on the nose bridge. By allowing the brow bar to pivot on the bridge pins 173, the brow bar will self align with the adjacent angle of the mask user's forehead.

The mask body 168 is provided with a plurality of notches 186 which are arranged in a row extending generally parallel to the slot 184. The notches 186 may be spaced in a plane or along a slightly curved surface. The end 182 of the lock member 179 normally engages one of the notches 186 to lock the orientation of the bridge 169 relative to the mask body 168. When the knobs 183 are moved towards the bridge end 170, the lock member end 182 disengages the notches 186 to permit adjustment of the position of the bridge 169. The mask body 168 is shown with four notches 186 to allow four positions for the bridge 169. It will be appreciated that fewer or more notches 186 may be provided.

A pressurized gas inlet elbow 189 is mounted on the mask body 168 for rotation about an axis 190. Preferably, the axis 190 is generally perpendicular to a mask user's face, although the actual angle will vary with different mask users. The elbow 189 is connected to a pressurized gas hose (not shown) connected, for example, to the blower of conventional CPAP apparatus. The elbow 189 is free to rotate as the mask user changes positions, for example, during sleep. For some applications, it is desirable to route the gas hose to extend over the mask user's forehead. The gas hose may be connected in a known manner to the headgear which secures the mask to the user. An elbow lock 191 is mounted between the bridge arms 176 and the mask body 168 to pivot on the pins 177. When the elbow 189 is oriented to be directed towards the mask user's forehead, the elbow lock 191 may be pivoted to engage a notch 192 on the elbow to lock the position of the elbow 189. A plurality of notches 192 may be provided to accommodate different locations of the pins 177 for different bridge orientations.

It will be appreciated that various modifications and changes may be made to the above described preferred embodiments of a nasal mask without departing from the scope of the following claims.

The invention claimed is:

1. A nasal mask including a body, said body having an upper portion and a lower portion, a bridge extending from said upper portion of said body, said bridge having a free end, a brow bar, and means for releasably connecting said free end of said bridge to said brow bar, wherein said bridge includes first and second spaced apart resilient arms extending towards said free end of said bridge, said first arm has a first pin mounted adjacent a free end of said first arm, said second arm has a second pin mounted adjacent a free end of said second arm in axial alignment with said first pin, and wherein said means for releasably connecting said bridge to said brow bar comprises said first and second pins and at least one opening on said brow bar which receives said first and second pins when said bridge is connected to said brow bar, whereby said brow bar rotates on said first and second pins.

2. A nasal mask, as set forth in claim 1, and wherein said at least one opening on said brow bar comprises first and second axially aligned openings, said first opening receiving said first pin and said second opening receiving said second pin when said bridge is connected to said brow bar.

3. A nasal mask, as set forth in claim 2, and wherein said first and second openings are spaced apart to receive said free end of said bridge therebetween, and wherein said first and second pins have ends angled for deflecting said first and second resilient arms when said free end of said bridge is inserted into the space between said first and second openings.

4. A nasal mask, as set forth in claim 1, and further including headgear having elastic upper and lower straps, said lower strap being adapted in use to extend continuously around a user's head, said upper strap having two ends attached to said brow bar, and wherein said lower portion of said body includes a recess adapted to receive said lower strap to secure the lower portion of said mask to a user's head.

5. A nasal mask including a body, said body having an upper portion and a lower portion, a bridge extending from said upper portion of said body, said bridge having a free end, a brow bar, and means for releasably connecting said free end of said bridge to said brow bar, and including means mounting said bridge on said body to move between a plurality of positions, and further including a lock mechanism for selectively locking said bridge to said body in any of a plurality of different positions, wherein said bridge includes first and second spaced apart resilient arms extending towards said free end of said bridge, said first and second arms each having a first pin mounted adjacent a free end of said first and second arms with said first pins axially aligned, said first and second arms each having a second pin spaced from said free ends of said first and second arm with said second pins in axial alignment, and wherein said means mounting said bridge on said body includes said first and second pins, and first and second pairs of spaced apart elongated grooves on said body, said first grooves extending parallel to each other and receiving said first pins, said second grooves extending parallel to each other and receiving said second pins, and wherein said first elongated grooves extend at an angle relative to said second elongated grooves.

6. A nasal mask, as set forth in claim 5, and wherein when said mask is attached to a user's face, said first grooves extend generally parallel to the user's face and said second grooves extend generally perpendicular to the user's face.

7. A nasal mask, as set forth in claim 5, and including a plurality of spaced notches on said mask body, and wherein said lock mechanism selectively engages at least one of said notches to lock an angular position of said bridge relative to said body.

8. A nasal mask, as set forth in claim 7, and wherein said notches are spaced in a direction generally parallel to said second grooves.

* * * * *